(12) United States Patent
McIntyre et al.

(10) Patent No.: US 7,883,506 B2
(45) Date of Patent: Feb. 8, 2011

(54) DEVICES AND METHODS FOR THE TREATMENT OF ENDOMETRIOSIS

(75) Inventors: Jon T. McIntyre, Newton, MA (US);
Francis P. Grillo, Wellesley, MA (US);
Isaac Ostrovsky, Wellesley, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 702 days.

(21) Appl. No.: 11/262,459

(22) Filed: Oct. 28, 2005

(65) Prior Publication Data

US 2006/0100615 A1     May 11, 2006

Related U.S. Application Data

(60) Provisional application No. 60/626,033, filed on Nov. 8, 2004.

(51) Int. Cl.
*A61B 18/04* (2006.01)
*A61B 8/00* (2006.01)

(52) U.S. Cl. .......................................... 606/27; 600/439

(58) Field of Classification Search ................. 600/439; 601/2, 3; 606/2, 3, 27
See application file for complete search history.

(56) References Cited

U.S. PATENT DOCUMENTS

| | | | |
|---|---|---|---|
| 4,660,573 A | 4/1987 | Brumbach | |
| 4,899,733 A | 2/1990 | DeCastro et al. | |
| 5,368,558 A * | 11/1994 | Nita | 604/22 |
| 5,676,635 A * | 10/1997 | Levin | 600/120 |
| 5,971,918 A | 10/1999 | Zanger et al. | |
| 6,214,023 B1 * | 4/2001 | Whipple et al. | 606/169 |
| 6,514,203 B2 * | 2/2003 | Bukshpan | 600/439 |
| 6,626,855 B1 | 9/2003 | Weng et al. | |
| 6,658,279 B2 * | 12/2003 | Swanson et al. | 600/407 |

FOREIGN PATENT DOCUMENTS

EP      0 659 387      6/1995

OTHER PUBLICATIONS

Löning Martin et al., "Laparoscopic Fluorescence Detection of Ovarian Carcinoma Metastases Using 5-Aminolevulinic Acid-Induced Protoporphyrin IX", vol. 100, No. 8, Apr. 15, 2004, pp. 1650-1656.

* cited by examiner

*Primary Examiner*—Lee S Cohen
(74) *Attorney, Agent, or Firm*—Fay Kaplun & Marcin, LLP

(57) ABSTRACT

A tissue treatment device comprises an insertion sized and shaped for insertion into the body via a trocar and a diagnostic element coupled to the insertion section, the diagnostic element illuminating tissue with the light of a wavelength selected to facilitate identification of target tissue in combination with an ultrasound element coupled to the insertion section for delivering to a portion of tissue illuminated by the diagnostic element ultrasound energy.

19 Claims, 2 Drawing Sheets

US 7,883,506 B2

DEVICES AND METHODS FOR THE TREATMENT OF ENDOMETRIOSIS

PRIORITY CLAIM

This invention claims priority to U.S. Provisional Patent Application Ser. No. 60/626,033 entitled "Devices and Methods for the Treatment of Endometriosis" filed Nov. 8, 2004, the disclosure of which is incorporated, in its entirety, herein.

BACKGROUND OF THE INVENTION

The rate of recurrence for endometriosis is high. This is partially due to difficulties in diagnosing and removing the implanted endometrial tissue.

A first step in localized treatments is the identification of endometrial lesions on the walls of the peritoneal cavity. Once the lesions have been located, these areas may be treated for removal thereof. For example, heat, electricity, cold, or radiation may be directed to each of the lesions to necrose the tissue. Alternatively, the tissue may be excised or removed by another mechanism. The effectiveness of these methods depends generally on the accuracy of the localization of the lesions and the accuracy with which the therapeutic treatment is provided to those locations.

Blue light (e.g., of approximately 440 nm in wavelength, but that may range from 400 to 500 nm) has been shown to be superior to white light in identifying endometriosis lesions. Current treatments generally involve the insertion of a laparoscope to an operative space (e.g., via a first trocar) and the insertion into the operative space of a second trocar for the introduction of diagnostic and therapeutic tools. To supplement the white light source of the vision system of the laparoscope, a source of diagnostic light (e.g., blue light) is inserted into the operative space via the second trocar to identify target tissue (e.g., lesions) and to physically mark the locations of this target tissue. The source of diagnostic light is then removed from the second trocar and a source of ablation energy (e.g., radio frequency energy, laser energy) is introduced through the second trocar into the operative space. Energy from the energy source is then directed to the positions earlier noted for target tissue. It is difficult to apply the treatments to the exact locations of the lesions using this method as the bleeding associated with the current treatments (e.g., laser or RF ablation) interferes with the observation of the target locations. In addition, the time required for these treatments is increased as the diagnostic light source is withdrawn and the energy source is inserted.

SUMMARY OF THE INVENTION

In one aspect, the present invention is directed to a tissue treatment device comprising an insertion section sized and shaped for insertion into the body via a trocar and a diagnostic element coupled to the insertion section, the diagnostic element illuminating tissue with light of a wavelength selected to facilitate identification of target tissue in combination with an ultrasound element coupled to the insertion section for delivering ultrasound energy to a portion of tissue illuminated by the diagnostic element.

DETAILED DESCRIPTION

Figure 1:
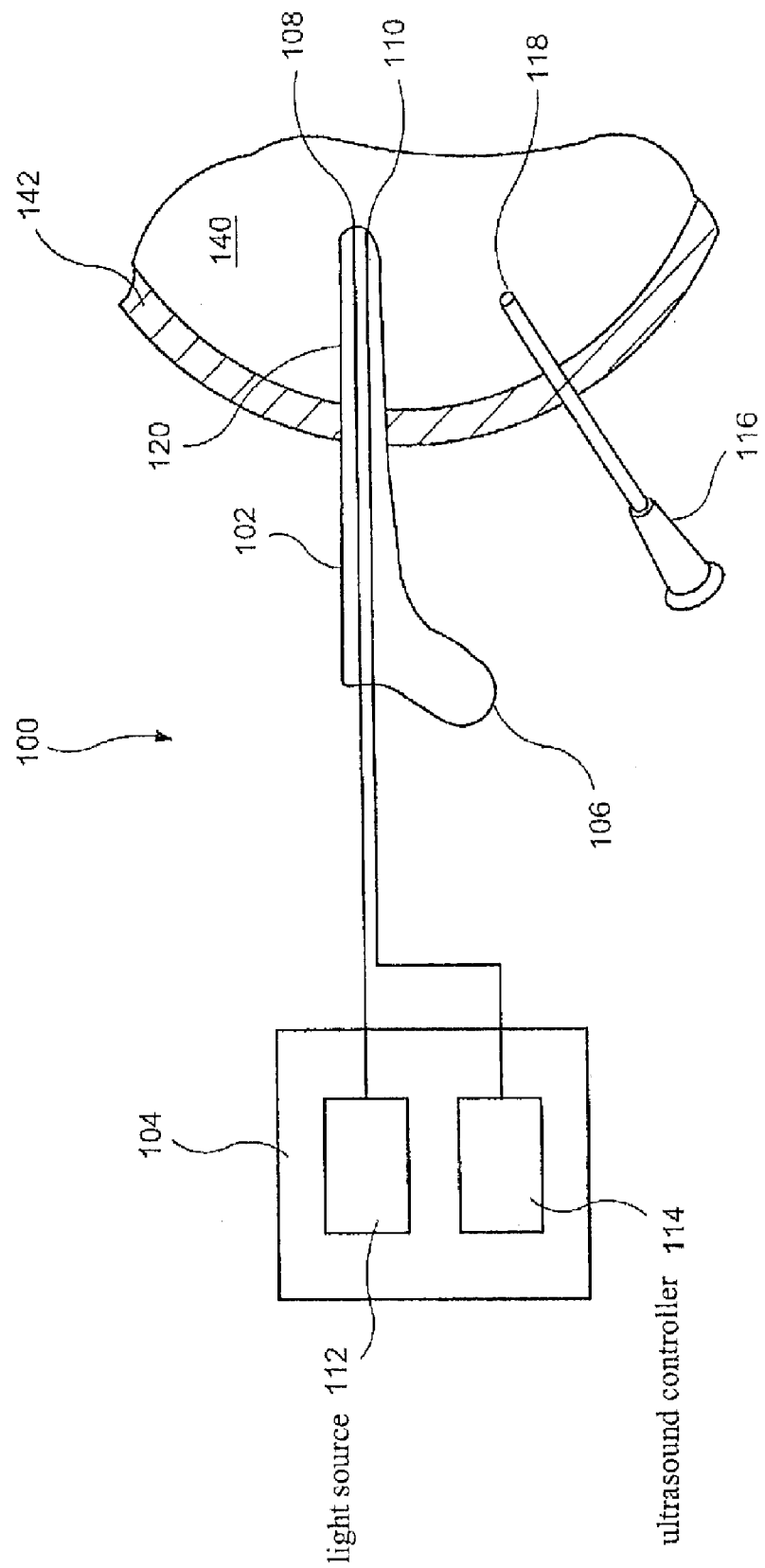
FIG. 1 is a diagram showing a first embodiment of a treatment system according to the present invention.

The present invention may be further understood with reference to the following description and the appended drawings, wherein like elements are referred to with the same reference numerals. The invention relates to devices for the treatment of tissue within body spaces or hollow organs and more specifically relates to a system and method for minimally invasively surgically treating endometriosis and other lesions.

Embodiments of the present invention simplify the treatment of tissue in hollow organs and make these treatments more reliable. An exemplary system according to embodiments of the present invention integrates a diagnostic light and an ultrasound energy source into a single tool permitting a user to accurately identify and treat target tissue under visual guidance. Thus, the surgeon is able to accurately aim energy from the ultrasound source toward each portion of target tissue under visual control while illuminated by the diagnostic light source. According to an exemplary embodiment of the invention, a user may switch back and forth between differing illumination modes (e.g., blue and white light) without removing and re-introducing devices or illumination sources and without requiring an additional trocar. In another embodiment, a user may use both the blue light and the white light at the same time.

Procedures using embodiments of the present invention are no more invasive than conventional procedures as the diagnostic light source and the ultrasound energy source are incorporated into a single tool and no additional incisions or trocars are required. Furthermore, the ultrasound energy delivery device incorporated in the embodiments of the present invention minimizes the interference with vision associated with the bleeding caused by other treatment methods and makes it possible to maintain the target tissue under visual observation with either blue or white light during tissue treatment. It will be apparent to those of skill in the art that the exemplary surgical device may be used for other procedures in addition to the treatment of endometriosis. For example, interstitial cystitis may also benefit from a treatment utilizing a tool including a light source and an ultrasound energy delivery device as will be described in more detail below.

As shown in FIG. 1 a system 100 according to an exemplary embodiment of the invention includes an integrated diagnostic and therapeutic handpiece 102 including apparatus for identifying and treating target tissue (e.g., lesions) within a body space or cavity. For example, the treatment may include subjecting target tissue to ultrasound energy to, for example, ablate the tissue. A control unit 104 contains remote components of the diagnostic and ultrasound devices. For example, generators and electronic controls too large or otherwise unsuitable for location in the handpiece 102 are preferably housed in the control unit 104. A conventional laparoscope 116 containing a vision tool 118 including a source of white light and a conventional light gathering apparatus is used to provide a view of the handpiece 102 during the procedure to aid the user in guiding and positioning the handpiece 102. Typically, the laparoscope 116 is inserted into the body space 140 via a second incision, or through a trocar. Those skilled in the art will understand that, for certain procedures, a flexible endoscope may be substituted for the laparoscope 116 and that the flexible endoscope may be inserted into the hollow organ via an incision or through a naturally occurring body orifice.

In one embodiment, the handpiece 102 is formed as a disposable element including only those components necessary to illuminate and deliver ultrasound energy to the target tissue. For example, a light guide such as an optic fiber may be used to convey light from a light source located within the control unit 104 to an illumination element 108. The ultrasound component 110 is mounted to the insertion element 120 so that it may be placed against tissue at which light from the illumination element 108 is aimed to directly transfer ultrasound energy thereto. For such a disposable item, the more expensive components of the system 100, for example, the light source 112 and an ultrasound controller 114 are preferably located in the control unit 104 which is not disposable.

The handpiece 102 preferably comprises a component 106 ergonomically shaped to facilitate grasping and manipulation by a user. An insertion element 120 of the handpiece 102 is adapted for insertion into a body space 140, for example, through the abdominal wall 142. The body space 140 may, for example, be a hollow organ or space such as the peritoneal cavity. In the exemplary embodiment, the handpiece 102 comprises an illumination element 108 directing light toward a target area to assist in identifying lesions on the wall of the hollow organ. The handpiece 102 also includes an ultrasound component 110 directing ultrasound energy to the target area illuminated by the illumination element 108.

The illumination element 108 includes, for example, a light guide such as an optic fiber extending along the length of the handpiece 102 and operatively connected to a light source 112 located within control unit 104. The light source 112 may, for example, be a low power bulb, diode, or other conventional surgical source of illumination. The frequency of the light emitted is preferably selected to facilitate the diagnostic procedure for the particular type of target tissue being treated. For example, blue light, for example in the wavelength range of about 440 nm has been found to be suitable where the target tissue, is endometriosis lesions. Those skilled in the art will understand that a control unit that includes the ability to change light spectrum on command (e.g., blue light to white light) in addition to delivering therapeutic energy may also be advantageous. This may be done in any number of ways including using a source of white light for the light source 112 and moving a filter in and out of a path of the light, switching between the illumination element 108 and an illumination element of the laparoscope 116, endoscope, etc. or by incorporating at the distal end of the insertion element 120 a separate white light illumination element coupled to a separate light source.

The ultrasound component 110 which is, for example, a single, small diameter ultrasound crystal mounted on a distal end of the insertion element 120 is vibrated under control of the ultrasound controller 114 as would be understood by those skilled in the art to generate ultrasound energy of a desired frequency to tissue against which it is abutted. The ultrasound controller may for example comprise a microprocessor or other computing device controlling signals output from a power source to vibrate an ultrasonic crystal at a desired frequency and amplitude as would be understood by those skilled in the art. The ultrasound component 110 is preferably an ultrasound crystal 10 mm or less in diameter and, more preferably, 8 mm or less in diameter so that the insertion element 120 may be inserted through trocars of as little as 10 mm I.D. Alternatively, the ultrasound component 110 may include an array of ultrasound crystals and may further include an ultrasound dome disposed over the ultrasound component 110 and filled with a coupling medium (e.g., water) allowing ultrasonic waves to propagate therethrough to the lesion when the ultrasound dome is pressed thereagainst. As would be understood by those skilled in the art, the level of ultrasound energy delivered to a lesion may be determined as a function of power supplied to the ultrasound component 110 and/or a time for which the ultrasound component 110 is in contact with the lesion.

As little or no bleeding occurs during this ultrasound ablation, the user is able to immediately move to another lesion after a desired degree of treatment of a first lesion has been achieved. In this case, the energy supply to the ultrasound component 110 is suspended, the hand piece 102 is moved to separate the ultrasound component 110 from the first lesion and, under visual guidance using, for example, the blue light from the illumination element 108, the ultrasound component 110 is moved into contact with a second lesion and the process is repeated until all the lesions have been treated to the desired degree.

According to exemplary embodiments of the invention, low power diagnostic light from the illumination element 108 is used to illuminate a target portion of tissue to assist the user in aiming the ultrasound component 110. Accordingly, the low power light and the ultrasound energy are aimed so that they converge on the same target spot allowing the user to aim the ultrasound energy on the tissue to be treated. That is, the target spot illuminated by the illumination element 108 is the same as or substantially aligned with the target spot that the ultrasound energy will be incident upon when the ultrasound component 110 is pressed to the tissue. The illumination element 108 preferably illuminates an area larger than that on which the energy from the ultrasound component 110 is focused with the ultrasound energy focused, for example, at a center of the spot illuminated by the illumination element 108. Thus, the user may identify a lesion and immediately treat the lesion by merely switching on the ultrasound component 110 with no reconfiguration of the hardware required. As described above, since both the illumination element 108 and the ultrasound component 110 are integrated in the handpiece 102, the procedure remains minimally invasive requiring only two incisions.

Figure 2:
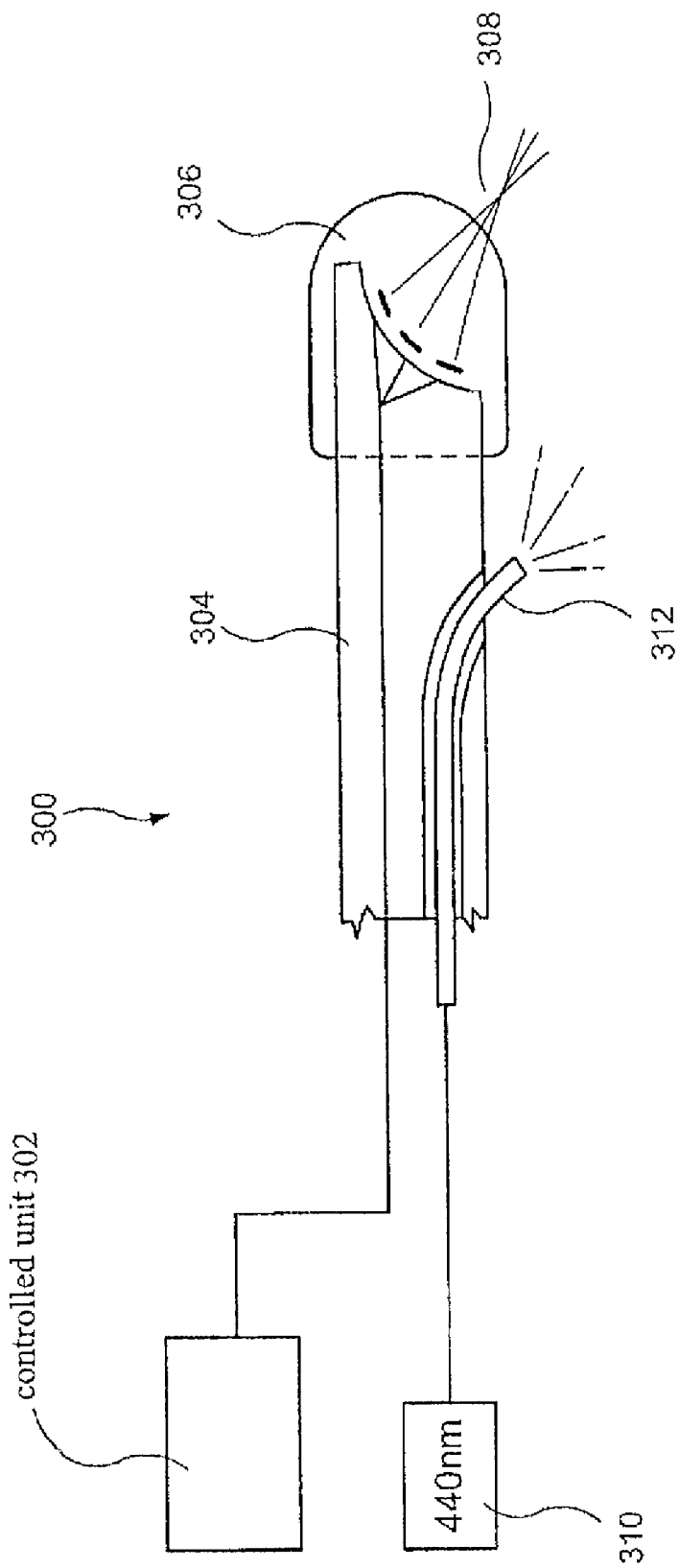
FIG. 2 is a diagram showing a second embodiment of a treatment system according to the present invention.

As shown in FIG. 2, a system 300 according to a second embodiment of the present invention includes an array of ultrasonic crystals 308 focusing ultrasonic energy on a target lesion illuminated by a diagnostic component 312 receiving light from a light source 310. For example, an ultrasound control unit 302 is operatively connected to a distal portion of the handpiece 304 with an ultrasound dome 306 disposed at the distal tip of the handpiece 304 containing the array of ultrasound crystals 308. As would be understood by those skilled in the art, energy from these crystals 308 may be focused on a specific spot based on operating commands from the control unit 302 by, for example, controlling the frequency, phase and intensity of the signals from the various crystals 308 to shape and focus the sound beam as desired. Alternatively, energy from the crystals 308 may be focused on a specific spot by simply arranging the crystals 308 along a curved surface having a focus area (e.g., a focus point or path) within an area illuminated by the diagnostic component 312. The light source 310 which preferably produces white and/or blue light, is connected operatively to the diagnostic component 312 to illuminate the target portion of tissue.

In one exemplary embodiment, the handpiece 102 has a diameter of less than 9 mm and is more preferably less than 5 mm in diameter to facilitate insertion into a hollow organ or other body space through a first trocar of, for example, 5 mm or 10 mm diameter. Furthermore, the system according to the invention is preferably designed for use in laparoscopic procedures where a laparoscope is inserted into the body through a second trocar of, for example, of 5 mm or 10 mm diameter.

The present invention has been described with reference to specific embodiments, and more specifically to an endometrial treatment system. However, other embodiments may be devised that are applicable to other medical procedures, and which utilize other sources of therapeutic energy, without departing from the scope of the invention. Accordingly, various modifications and changes may be made to the embodiments, without departing from the broadest spirit and scope of the present invention as set forth in the claims that follow. The specification and drawings are accordingly to be regarded in an illustrative rather than restrictive sense.

What is claimed is:

1. A tissue treatment device, comprising:
an insertion section sized and shaped for insertion into the body via a trocar;
a diagnostic element coupled to the insertion section, the diagnostic element illuminating tissue with light of a wavelength selected to facilitate identification of a target portion of tissue; and
an ultrasound element including a generating component coupled to the insertion section and exposed to an exterior thereof so that the generating component may be positioned against the target portion of tissue, the generating component generating ultrasound energy for direct delivery to the target portion of tissue.

2. The device according to claim 1, further comprising a control unit coupled to the diagnostic element and the ultrasound element, the control unit remaining outside of the body space while the insertion section is inserted into the body.

3. The device according to claim 2, wherein the ultrasound element is coupled to an ultrasound controller located in the control unit.

4. The device according to claim 3, wherein the diagnostic element includes a light source.

5. The device according to claim 4, wherein the light source is one of a low-power bulb and a diode.

6. The device according to claim 1, wherein the light is one of white light and blue light.

7. The device according to claim 1, wherein the generating component includes at least one ultrasonic crystal.

8. The device according to claim 7, wherein the at least one ultrasonic crystal has a diameter of no more than approximately 10 mm.

9. The device according to claim 1, wherein the insertion section has a diameter of about 5 mm to about 9 mm.

10. The device according to claim 1, wherein the diagnostic component and the generating component are aimed at a common target area so that light from the diagnostic component is aimed at the target area as the generating component is moved toward the target area.

11. A method for tissue treatment, comprising:
inserting into a body space an endoscopic element;
illuminating tissue with a wavelength of light selected to facilitate identification of a particular type of target tissue via an integrated illumination element of the endoscopic element; and
placing a generating component of an ultrasound element in contact with an identified portion of target tissue, the generating component generating ultrasound energy and directly delivering the ultrasound energy to the identified portion of target tissue.

12. The method according to claim 11, wherein the illumination element is aimed so that, during movement of the generating component into contact with a first target portion of tissue, the illumination element illuminates the first target portion of tissue.

13. The method according to claim 12, further comprising the steps of: delivering ultrasound energy to the first target portion of tissue while the generating component is in contact with the first target portion of tissue; and upon completion of the delivery of energy to the first portion of target tissue, moving the generating component away from the first portion of target tissue to contact a second portion of target tissue while illuminating the second portion of target tissue with the illumination element.

14. A device comprising:
a diagnostic component illuminating a target portion of tissue within a body space;
an ultrasound component including a generating component exposed to an exterior thereof so that the generating component may be positioned against the target portion of tissue, the generating component generating ultrasound energy for direct delivery to the target portion of tissue; and
a control unit coupled to the diagnostic component and the ultrasound component, the control unit remaining outside of the body space,
wherein operative ends of the diagnostic component and the ultrasound component are aimed at the target portion of tissue so that light from the diagnostic component is aimed at the target portion of tissue while the generating component is moved into contact therewith.

15. The device according to claim 14, wherein the diagnostic and generating components are mounted on a distal end of an insertion section of the device, the insertion section extending distally from a handle portion which, while the insertion section is inserted into the body, remains outside the body.

16. The device according to claim 14, wherein the light from the diagnostic component is approximately 440 nm in wavelength.

17. The device according to claim 14, wherein the generating component comprises a single ultrasound crystal with a diameter of no more than about 10 mm.

18. The device according to claim 17, wherein the generating component comprises a single ultrasound crystal with a diameter of no more than about 8 mm.

19. The device according to claim 14, wherein the generating component comprises an array of ultrasound crystals.

* * * * *